United States Patent [19]

Corey et al.

[11] Patent Number: 5,728,732
[45] Date of Patent: Mar. 17, 1998

[54] SKIN TREATMENT WITH SALICYLIC ACID ESTERS AND RETINOIDS

[75] Inventors: Joseph Michael Corey, Waterbury; Angel Augusto Guerrero, Huntington, both of Conn.

[73] Assignee: Elizabeth Arden Company, Division of Conopco, Inc., New York, N.Y.

[21] Appl. No.: 757,784

[22] Filed: Nov. 27, 1996

[51] Int. Cl.$^6$ .................................................. A61K 7/42
[52] U.S. Cl. .................... 514/544; 514/546; 514/549; 514/725
[58] Field of Search .................. 514/544, 725, 514/546, 549

[56] References Cited

U.S. PATENT DOCUMENTS

| | | |
|---|---|---|
| 4,603,146 | 7/1986 | Kligman . |
| 4,877,805 | 10/1989 | Kligman . |
| 4,891,227 | 1/1990 | Thaman et al. . |
| 4,891,228 | 1/1990 | Thaman et al. . |
| 5,262,407 | 11/1993 | Leveque et al. . |

FOREIGN PATENT DOCUMENTS

| | | |
|---|---|---|
| 0 713 696 | 10/1994 | European Pat. Off. . |
| 0 676 194 | 10/1995 | European Pat. Off. . |
| 4 036 238 | of 0000 | Japan . |
| WO 93/10755 | 6/1993 | WIPO . |
| WO 93/10756 | 6/1993 | WIPO . |

OTHER PUBLICATIONS

Product Brochure—Vevy Europe, BTNA (1991).
Product Brochure—Lexicon Vevy Europe, Skin Care Instant Reports (1990).
Elizabeth Arden "SPA Comeback Cream"—(1994) carton with ingredient listing including tridecyl salicylate.
Kang et al Journal of Investigative Dermatology, Inc., pp. 359–556 (1995) "Application of Retinol to Human Skin In Vivo Induces Epidermal Hyperplasia and Cellular Retinoid Binding Proteins Characteristic of Retinoic Acid but Without Measurable Retinoic Acid Levels or Irritation".

*Primary Examiner*—Rebecca Cook
*Attorney, Agent, or Firm*—Milton L. Honig

[57] ABSTRACT

A method and composition is provided for treating skin conditions including those arising from dermatologic disorders, chronoaging and environmental abuse. Non-ring esterified $C_{11}$–$C_{30}$ alkyl or alkenyl esters of salicylic acid in combination with a retinol $C_{18}$–$C_{30}$ fatty acid ester used as the active components are applied to the skin in a pharmaceutically acceptable carrier. Most preferred as the salicylate ester is tridecyl salicylate and as the retinol fatty acid ester is retinyl linoleate.

10 Claims, No Drawings

SKIN TREATMENT WITH SALICYLIC ACID ESTERS AND RETINOIDS

BACKGROUND OF THE INVENTION

1. Field of the Invention

The present invention concerns methods of treating skin with compositions containing certain esters of salicylic acid and retinoids.

2. The Related Art

Skin is subject to deterioration through dermatologic disorders or normal aging (chronoaging) as well as extrinsic factors (environmental). Dermatologic disorders include such conditions as acne, dry skin, dandruff, keratosis, pruritus, inflammatory dermatoses, eczema, psoriasis and tenia pedis (athlete's foot).

Chronoaging results in the thinning and general degradation of skin. As skin naturally ages, there is reduction in the cells and blood vessels that supply the skin. There is also a flattening of the dermal-epidermal junction which results in weaker mechanical resistance. Older individuals increasingly develop facial fine lines, wrinkles, leatheriness, yellowing, sagging, mottling (hyperpigmentation), age spots and the general signs of aging.

Extrinsic factors are primarily those caused by exposure to sun. Changes are most prominent in light skinned individuals who burn easily and tan poorly. The results of photodamage may be identical to those of aging except appearing at an accelerated rate. Wrinkling, yellowing, leatheriness, mottling and hyperpigmentation are all associated with sun damage. Most disturbing to many individuals is the wrinkling effect. It is a prime reminder of the disappearance of youth. As a result, there have been many reports of cosmetic treatments aimed at the elimination of wrinkles.

PCT applications WO 93/10755 and WO 93/10756 report salicylic acid as an effective anti-wrinkling agent. U.S. Pat. No. 5,262,407 reports use of ring acylated salicylic acid as a treatment against skin aging. Salicylic acid has also been described for the treatment of acne in U.S. Pat. No. 4,891,227 and U.S. Pat. No. 4,891,228. Moreover, salicylic acid has been used for the removal of warts, corns and calluses; for the treatment of psoriasis, seborrheic dermatitis and dandruff; and for the topical treatment of ringworm infection. A listing of commercially available products containing salicylic acid will be found in the Physician's Desk Reference, 45th Edition, 1991, page 323.

Ring alkylated salicylic acid has been reported in Japanese Patent 4036238 (Takasago Perfumery KK) for treatment of ache vulgaris.

Significant irritation is often associated with the use of salicylic acid. Another problem is that salicylic acid is not always readily formulatable into oily compositions. Derivatives of salicylic acid most often leave the acidic function free. Irritation caused by acidity is therefore not prevented by such derivatives.

Skin care compositions containing retinoids have also become quite prominent in recent years. Retinoic acid, also known as Vitamin A acid or Tretinoin, is well known for treatment of acne. Even more recently, the retinoids have been suggested as treatment against photoaging and sun damage. For instance, U.S. Pat. No. 4,603,146 discloses Vitamin A acid in an emollient vehicle to prevent skin aging. U.S. Pat. No. 4,877,805 suggests a number of retinoids as useful for restoring and reversing sun damage in human skin. EP 0 631 772 describes use of retinol in combination with an irritation ameliorating amount of glycolic acid.

EP 0 676 194 describes cosmetic compositions containing a cocktail of an alpha-hydroxy acid, a salicylic acid or ester thereof and a retinoid. While various dermatological benefits are claimed for the cocktail, there is a need for further improvements.

Accordingly it is an object of the present invention to provide a treatment for a variety of dermatologic disorders such as acne, dry skin, dandruff, keratosis, pruritus, inflammatory dermatosis, eczema, psoriasis and tinea pedis.

Another object of the present invention is to provide a treatment for chronoaging conditions including wrinkling and fine lines, leatheriness, yellowing, sagging, mottling (hyperpigmentation), age spots and the general signs of aging.

Still another object of the present invention is to provide a treatment against environmental abuse to skin including wrinkling and fine lines, yellowing, leatheriness, mottling and hyperpigmentation.

Yet another object of the present invention is to provide a treatment to improve the condition of skin with a composition and active that does not impart irritation.

These and other objects of the present invention will become more readily apparent from the following summary and detailed discussion.

SUMMARY OF THE INVENTION

A cosmetic composition is provided including:

(i) a safe and effective amount of a salicylate ester having formula (I):

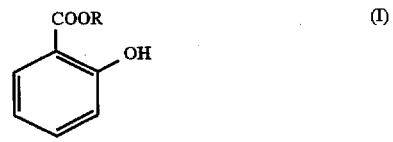

wherein R is a $C_{11}$–$C_{30}$ alkyl or alkenyl radical;

(ii) a safe and effective amount of a retinol $C_{18}$–$C_{30}$ fatty acid ester; and (iii) a safe and effective amount of a pharmaceutically acceptable carrier.

A method is also provided for treating skin conditions selected from the group consisting of dermatologic skin disorders, chronoaging, environmental abuse and combinations thereof, by applying to the skin a composition including as an active a combination of a retinol $C_{18}$–$C_{30}$ fatty acid ester and a salicylate ester having the structure (I):

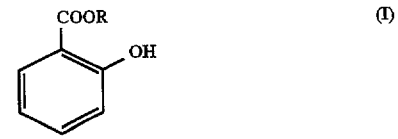

wherein R is a $C_{11}$–$C_{30}$ alkyl or alkenyl radical.

DETAILED DESCRIPTION OF THE INVENTION

Now it has been discovered that deterioration of skin through dermatologic disorders, chronoaging and environmental abuse (e.g. sun and wind) can be reduced, inhibited and even reversed through application of a cosmetic composition including as active a combination of a retinol $C_{18}$–$C_{30}$ fatty acid ester and a non-ring ester derivative of salicylic acid having formula (I):

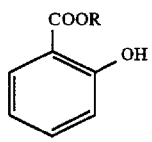

wherein R is a $C_{11}$–$C_{30}$ alkyl or alkenyl radical. Most preferred are the $C_{12}$–$C_{20}$, optimally the $C_{13}$ esters of salicylic acid.

Retinol $C_{18}$–$C_{30}$ fatty acid ester is one of the two actives essential for the method and compositions of the present invention. Vitamin A esters such as Vitamin A palmitate or acetate are not here effective and do not fall within the scope of this invention. Retinol esters which are effective include retinyl linoleate, retinyl linoleneate, retinyl oleate, retinyl stearate, retinyl behenate and mixtures thereof. Most preferred is retinyl linoleate.

"Safe and effective amounts" of the $C_{11}$–$C_{30}$ esters of salicylic acids and retinol and its esters are to be used within cosmetic compositions of the present invention. The term "safe and effective amounts" are defined as any amount sufficient to significantly induce a positive modification in the condition to be treated, but low enough to avoid serious side effects (at a reasonable benefit/risk ratio), within the scope of sound medical judgement. The safe and effective amount of the salicylate esters will vary with the particular condition being treated, the age and physical condition of the patient being treated, the severity of the condition, the duration of the treatment, the nature of concurrent therapy, the specific ester employed, the particular pharmaceutically-acceptable carrier utilized, and like factors in the knowledge and expertise of the attending physician. Generally the amounts of salicylate ester may range from 0.01 to 20%, preferably from 0.1 to 10%, more preferably from 1 to 8%, optimally from 2 to 6% by weight. Amounts of retinol or its esters may range from 0.01 to 10%, preferably from 0.1 to 5%, more preferably from 0.2 to 0.5% by weight.

Besides the retinol or ester thereof and salicylate ester, compositions of the present invention will utilize a pharmaceutically acceptable carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 25 to 40% by weight.

Emollient materials may also serve as pharmaceutically acceptable carriers. These maybe in the form of silicone oils and synthetic esters. Amounts of the emollients may range anywhere from 0.1 to 30%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Fatty acids having from 10 to 30 carbon atoms may also be included as pharmaceutically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as pharmaceutically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners may also be utilized as part of the pharmaceutically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenum, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the pharmaceutically acceptable carrier in amounts from 1 to 99.9%, preferably from 80 to 99% by weight.

Cosmetic compositions of the present invention may be in any form. These forms may include lotions, creams, roll-on formulations, mousses, aerosol and non-aerosol sprays and pad-applied formulations.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}-C_{20}$ fatty alcohol or acid hydrophobe condensed with from 2 to 100 moles of ethylene oxide or propylene oxide per mole of hydrophobe; $C_2-C_{10}$ alkyl phenols condensed with from 2 to 20 moles of alkylene oxide; mono- and di-fatty acid esters of ethylene glycol; fatty acid monoglyceride; sorbitan, mono- and di- $C_8-C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8-C_{20}$ acyl isethionates, $C_8-C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water. Illustrative water-soluble vitamins are Niacin, Vitamin $B_2$, Vitamin $B_6$, Vitamin C and Biotin. One source for Vitamin C is a product sold under the trademark of Vitazyme C available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Keratolytic agents such as $C_2-C_{25}$ α-hydroxy alkanoic acids may also be incorporated into compositions of this invention. Illustrative of this group of materials are glycolic, lactic, α-hydroxyoctanoic acids and salts thereof. The salts may be selected from alkalimetal, ammonium and $C_1-C_{20}$ alkyl or alkanolammonium counterions. Levels of α-hydroxyalkanoic acids may range from 0.001 to 10%, preferably between 0.2 and 1%, optimally between 0.4 and 0.5% by weight.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont.

Colorants, fragrances, opacifiers and abrasives may also be included in compositions of the present invention. Each of these substances may range from about 0.05 to about 5%, preferably between 0.1 and 3% by weight.

The following Examples will more fully illustrate embodiments of this invention. All parts, percentages and proportions referred to herein and in the appended claims are by weight unless otherwise indicated.

EXAMPLE 1

A skin cream formulation of the oil in water type according to the present invention is described in Table I.

TABLE I

| CHEMICAL | % W/W |
|---|---|
| Water | qs |
| Disodium EDTA | 0.10 |
| Polysorbate 40 | 1.00 |
| Propylene Glycol | 3.00 |
| Methylparaben | 0.25 |
| Tridecyl Salicylate | 5.00 |
| Retinol | 0.30 |
| Isopropyl Palmitate | 5.00 |
| Isostearyl Isostearate | 3.00 |
| Silicone 200/100 Fluid (Dimethicone) | 5.00 |
| Silicone 344 Fluid (Cyclomethicone) | 15.00 |
| Imidazolidinyl Urea | 0.20 |
| Sepigel 305 (Laureth-7, Polyacrylamide, Isoparaffin) | 3.00 |

EXAMPLE 2

Another skin cream formulation of the oil in water type according to the present invention is described in Table II.

TABLE II

| CHEMICAL | % W/W |
|---|---|
| Water | qs |
| Disodium EDTA | 0.10 |
| Butylene Glycol | 3.00 |
| Glycerin | 3.00 |
| Methylparaben | 0.25 |
| Tridecyl Salicylate | 5.00 |
| Retinyl Linoleate | 0.30 |
| Squalane | 1.00 |
| Shea Butter | 0.50 |
| Cetyl Alcohol | 1.50 |
| Octyl Palmitate | 2.00 |

TABLE II-continued

| CHEMICAL | % W/W |
|---|---|
| C12-C15 Alkyl Benzoate | 5.00 |
| Octyl Stearate | 2.00 |
| Silicone 344 Fluid (Cyclomethicone) | 2.00 |
| Imidazolidinyl Urea | 0.20 |
| Sepigel 305 (Laureth-7, Polyacrylamide, Isoparaffin) | 3.50 |

EXAMPLE 3

Still another skin cream formulation of the oil in water type according to the present invention is described in Table III.

TABLE III

| CHEMICAL | % W/W |
|---|---|
| Water | qs |
| Disodium EDTA | 0.10 |
| Butylene Glycol | 2.00 |
| Glycerin | 3.00 |
| Methylparaben | 0.25 |
| Tridecyl Salicylate | 5.00 |
| Retinol | 0.30 |
| Shea Butter | 0.50 |
| Cetyl Alcohol | 1.00 |
| PEG-100 Glycerol Monostearate | 4.00 |
| C12-15 Alkyl Benzoate | 6.00 |
| Tocopheryl Linoleate | 0.50 |
| Silicone 200 Fluid (Dimethicone) | 2.00 |
| Imidazolidinyl Urea | 0.20 |

EXAMPLE 4

A microemulsion formulation according to the present invention is described in Table IV.

TABLE IV

| CHEMICAL | % W/W |
|---|---|
| PPG-5-Ceteth-20 | 4.00 |
| PEG-40 Hydrogenated Castor Oil | 1.75 |
| Polyglyceryl-10 Decaoleate | 10.00 |
| PEG-8 Caprylic/Capric Glycerides | 10.00 |
| SDA Alcohol 40B | 12.00 |
| Isodecyl Neopentanoate | 16.00 |
| Glyceryl Trioctanoate | 8.00 |
| Cyclomethicone (DC 344 Fluid) | 8.00 |
| Propylparaben | 0.10 |
| Isostearic Acid | 2.50 |
| Tridecyl Salicylate | 5.00 |
| Retinyl Behenate | 0.30 |
| Phenoxyethanol | 0.30 |
| Deionized Water | qs |

EXAMPLE 5

A skin cream formulation of the water in oil type according to the present invention is described in Table V.

TABLE V

| CHEMICAL | % W/W |
|---|---|
| Cyclomethicone (DC 344 Fluid) | 12.00 |
| Dimethicone (DC 200/10 fluid) | 2.00 |
| Dimethicone Copolyol | 2.50 |
| Cetyl Dimethicone | 0.50 |

TABLE V-continued

| CHEMICAL | % W/W |
|---|---|
| C12-15 Alkyl Benzoate | 3.00 |
| Tridecyl Salicylate | 5.00 |
| Retinyl Linoleate | 0.10 |
| Glycerin | 3.00 |
| Propylene Glycol | 2.00 |
| Disodium EDTA | 0.10 |
| Methylparaben | 0.25 |
| Sodium Chloride | 1.20 |
| Phenoxyethanol | 0.20 |
| Deionized Water | qs |

EXAMPLE 6

An anhydrous serum formulation according to the present invention is described in Table VI.

TABLE VI

| CHEMICAL | % W/W |
|---|---|
| Sepigel 305 | 1.50 |
| SD Alcohol 40 B (200 proof) | 20.00 |
| Cyclomethicone (DC 344 Fluid) | 2.50 |
| Squalene | 1.00 |
| Octyl Isononanoate | 2.50 |
| Dimethicone (DC 200 Fluid | 5.20 |
| Isononyl Isononanoate | 30.00 |
| Butylene Glycol | 1.00 |
| Propylparaben | 0.10 |
| Tridecyl Salicylate | 5.00 |
| Retinol | 0.50 |
| Dimethiconol | 2.75 |

EXAMPLE 7

A sunscreen lotion formulation of the oil in water type according to the present invention is described in Table VII.

TABLE VII

| CHEMICAL | % W/W |
|---|---|
| Water | qs |
| Disodium EDTA | 0.10 |
| Butylene Glycol | 2.00 |
| Glycerin | 5.00 |
| Methylparaben | 0.25 |
| Tridecyl Salicylate | 5.00 |
| Retinyl Linoleneate | 0.10 |
| Octyl Methoxycinnamate | 7.50 |
| Benzophenone-3 | 2.50 |
| Shea Butter | 0.50 |
| Cetyl Alcohol | 1.50 |
| Octyl Palmitate | 2.00 |
| C12-15 Alkyl Bezoate | 2.00 |
| Silicone 200 Fluid (Dimethicone) | 1.00 |
| Imidazolidinyl Urea | 0.20 |
| Sepigel 305 (Laureth-7, Polyacrylamide, Isoparaffin) | 3.50 |

EXAMPLE 8

Dermatologic disorders, chronoaging and environmental abuse all have some relationship to sebum production. The present example reports an in vitro analysis of sebum suppression by use of a combination of salicylate ester and retinoid.

In Vitro Sebocyte Lipogenesis Assay

Human sebaceous glands were isolated from the nose of a male (age 60) and cultured using submerged tissue culture techniques (Bajor et al, *J. Invest. Dermatol.* 102:1994. P. 564). These sebocytes accumulate intracellular lipid droplets characteristic of mature human sebum.

Harvested and passaged sebocytes were added to each well of a 48 well tissue culture plate and incubated at 37° C. in the presence of 7.5% $CO_2$ for 14 days. The growth medium was changed three times per week. On the day of experimentation, the growth medium was removed and the sebocytes washed three times with phosphate buffered saline (PBS). Fresh PBS in 0.5 ml amount was added to each well and 10 microliters of active agent speculated to inhibit lipogenesis. Triplicate wells were utilized for each sample. Controls consisted of PBS, dimethyl sulfoxide (DMSO) used to solubilize the lipophilic compounds, and phenol red, a compound which possesses estrogen-like activity. The cultures were incubated at 37° C. 7.5% $CO_2$ for 30 minutes. Radioactive label was prepared by adding 100 ul of 14-C labelled acetic acid (Amersham, sodium salt, specific activity of 56 mCi/mmol) to 10 mL of 50 mM sodium acetate buffer. Then 50 ul was added to each well containing the sebocytes and active agents. The cultures were returned to the incubator for 4 hours. Thereafter the treatments and label were removed and the sebocytes rinsed three times with fresh PBS. Sebocytes were harvested and 10 microliters removed and set aside for protein assessment. The remaining samples containing the 14-C label were extracted and the label counted using a Beckman scintillation counter. Triplicates were performed for each sample.

For each 48 well tissue culture plate, 16 samples could be analyzed. Of these, 1 sample was reserved for PBS, 1 sample for DMSO, and 1 sample for phenol red leaving 13 remaining samples. When TDS was analyzed in the presence of other compounds, an additional set of wells was used for measuring the effects of TDS atone. When multiple 48 well plates were used. TDS was included in each plate.

TABLE VIII

| Retinyl Linoleate Concentration | Retinyl Linoleate % Actual Reduction (SD) | Retinyl Linoleate + 10 uM TDS % Actual Reduction (SD) | Retinyl Linoleate + 10 uM TDS Theoretical (Additive) Reduction |
|---|---|---|---|
| 100 nM | 4.4 (2.9) | 21.1 (10.8) | 24.1 |
| 1 uM | 6.0 (19.5) | 26.1 (8.8) | 25.7 |
| 10 uM | 13.8 (7.6) | 50.0 (2.1) | 33.5 |
| 100 uM | 20.3 (3.3) | 41.5 (6.7) | 40.0 |

10 uM TDS = 19.7% Reduction

TABLE IX

| Retinyl Linoleate Conc. | Retinyl Linoleate % Actual Reduction (SD) | Retinyl Linoleate + 100 uM TDS % Actual Reduction (SD) | Retinyl Linoleate + 100 uM TDS % Theoretical (Additive) Reduction | Retinyl Linoleate + 50 uM TDS % Actual Reduction (SD) | Retinyl Linoleate + 100 uM TDS % Theoretical (Additive Reduction) |
|---|---|---|---|---|---|
| 10 uM | −15.0 (2.8) | −11.1 (35.9) | 15.8 | 5.3 (5.4) | 2.9 |
| 50 uM | −7.4 (4.3) | 39.1 (11.4) | 23.4 | 24.6 (2.2) | 10.5 |
| 100 uM | 1.9 (2.2) | 42.0 (9.4) | 32.7 | 36.1 (5.9) | 19.8 |

50 uM TDS = 17.9% Reduction
100 uM TDS = 30.8% Reduction

TABLE X

| Retinyl Palmitate Concentration | Retinyl Palmitate % Actual Reduction (SD) | Retinyl Palmitate + 100 uM TDS % Actual Reduction (SD) | Retinyl Palmitate + 100 uM TDS % Theoretical (Additive) Reduction |
|---|---|---|---|
| 10 uM | 12.2 (6.4) | 51.8 (7.1) | 50.9 |
| 100 uM | 12.0 (13.3) | 51.8 (5.2) | 50.7 |

100 uM TDS = 38.7% Reduction

From the foregoing Tables it is evident that retinyl linoleate appears to have a synergistic activity with tridecyl salicylate. By contrast, retinyl palmitate exhibited only an additive effective. Retinol was at very low levels synergistic with tridecyl salicylate.

The foregoing description and examples illustrate selected embodiments of the present invention. In light thereof, various modifications will be suggested to one

What is claimed is:

1. A cosmetic composition comprising:
   (i) a safe and effective amount of a salicylate ester having formula (I):

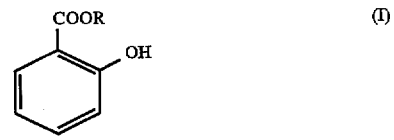

wherein R is a $C_{11}$–$C_{30}$ alkyl or alkenyl radical;
   (ii) a safe and effective amount of a retinol $C_{18}$–$C_{30}$ fatty acid ester; and
   (iii) a safe and effective amount of a pharmaceutically acceptable carrier.

2. The cosmetic composition according to claim 1 wherein the salicylate ester is a $C_{12}$–$C_{20}$ alkyl ester of salicylic acid.

3. The cosmetic composition according to claim 1 wherein the salicylate ester is tridecyl salicylate.

4. The cosmetic composition according to claim 1 wherein the retinol fatty acid ester is retinyl linoleate.

5. A method for treating skin conditions selected from the group consisting of acne, dry skin, dandruff, keratosis, pruritus, inflammatory dermatitis, eczema, psoriasis, tinea pedis, wrinkling, leatheriness, yellowing, sagging, mottling and age spots, the method comprising applying to the skin a safe and effective amount of a combination of a retinol $C_{18}$–$C_{30}$ fatty acid ester and a salicylate ester, the salicylate ester having the formula (I):

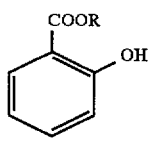 (I)

wherein R is a $C_{11}$–$C_{30}$ alkyl or alkenyl radical.

6. The method of claim 5 wherein the skin conditions are selected from the group consisting of acne, dry skin, dandruff, keratosis, pruritus, inflammatory dermatitis, eczema, psoriasis and tinea pedis.

7. The method according to claim 5 wherein the skin conditions are selected from the group consisting of wrinkling, leatheriness, yellowing, sagging, and age spots.

8. The method according to claim 5 wherein R is a $C_{12}$–$C_{20}$ alkyl or alkenyl group.

9. The method according to claim 5 wherein the salicylate ester is tridecyl salicylate.

10. The method according to claim 5 wherein the retinol fatty acid ester is retinyl linoleate.

* * * * *